United States Patent
Himmler et al.

(10) Patent No.: US 6,255,335 B1
(45) Date of Patent: Jul. 3, 2001

(54) SUBSTITUTED 2-OXO-ALKANOIC ACID-[2-(INDOL-3-YL)-ETHYL] AMIDES

(75) Inventors: Thomas Himmler, Odenthal; Franz Pirro, Langenfeld, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/673,155
(22) PCT Filed: Mar. 3, 1999
(86) PCT No.: PCT/EP99/02302
§ 371 Date: Oct. 11, 2000
§ 102(e) Date: Oct. 11, 2000
(87) PCT Pub. No.: WO99/54301
PCT Pub. Date: Oct. 28, 1999

(30) Foreign Application Priority Data

Apr. 16, 1998 (DE) ................................ 198 16 780

(51) Int. Cl.$^7$ ...................... A61K 31/404; C07D 209/18
(52) U.S. Cl. ............................... 514/419; 548/496
(58) Field of Search ............................ 548/496; 514/419

(56) References Cited

U.S. PATENT DOCUMENTS

| 3,217,011 | 11/1965 | Zenitz | 260/294.3 |
| 5,569,668 | 10/1996 | Webster et al. | 514/419 |

OTHER PUBLICATIONS

Chemistry & Industry, Feb. 1997, pp. 131–135, Steven J. Brickner, Multidrug–resistant Bacterial infections: driving the search for new antibiotics.

Drug Discovery Today, Feb. 1997, No. 2, Growing threat of Gram–positive resistance–a Challenge to the industry, pp. 47–49.

*L. Jianxiong et al, Synthesis and Antistaphylococcal Activity of Nematophin and Its Analogs, Bioorganic & Medicinal Chemistry Letters, vol. 7, No. 10, May 20, 1997, pp. 1349–1352, XP004136322.

*Himmler et al, "Synthesis and Antibacterial in Vitro Activity of Novel Analogues of Nematophin" Bioorganic & Medicinal Chemistry Letters, vol. 8, No. 15, Aug. 4, 1998, pp. 2045–2050, XP004137183.

*Primary Examiner*—Fiona T. Powers
(74) *Attorney, Agent, or Firm*—Joseph C. Gil; Godfried R. Akorli

(57) ABSTRACT

The invention relates to novel N-[2-(indol-3-yl)ethyl]-2-oxo-alkanarnides of the general formula (I)

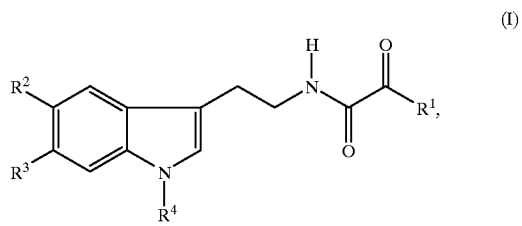

in which $R^1$ represents optionally branched $C_1$–$C_8$-alkyl or $C_4$–$C_8$-cycloalkyl, $R^2$ independently of $R^3$ represents hydrogen, $C_1$–$C_4$-alkyl, $C_1$–$C_4$-alkoxy, $C_1$–$C_4$-thioalkyl, phenyl or halogen, $R^3$ represents hydrogen, $C_1$–$C_4$-alkyl or halogen and $R^4$ represents optionally branched $C_1$–$C_6$-alkyl, $C_4$–$C_6$-cycloalkyl, phenyl which is optionally mono- to trisubstituted by $C_1$–$C_3$-alkyl, $C_1$–$C_3$-alkoxy, $C_1$–$C_3$-thioalkyl, halogen, nitro or amino or benzyl which is optionally mono- to trisubstituted by $C_1$–$C_3$-alkyl, $C_1$–$C_3$-alkoxy, $C_1$–$C_3$-thioalkyl, halogen, nitro or amino, to processes for their preparation and to their use in antibacterial compositions.

7 Claims, No Drawings

SUBSTITUTED 2-OXO-ALKANOIC ACID-[2-(INDOL-3-YL)-ETHYL] AMIDES

The invention relates to novel substituted N-[2-(indol-3-yl)-ethyl]-2-oxo-alkanamides, to processes for their preparation and to antibacterial compositions comprising them.

U.S. Pat. No. 5,569,668 discloses certain N-[2-(1H-indol-3-yl)-ethyl]-2-oxo-alkanamides and their antimycotic and antibacterial properties, in particular against staphylococci. A compound named nematophin, which is a natural compound formed by the bacterium *Xenorhabdus nematophilus*, is particularly emphasized. The action and properties of nematophin and certain derivatives have also been disclosed in Bioorganic & Medicinal Chemistry Letters, 7 (1997) 1349–1352.

The ever increasing number of multiresistant bacterial pathogens makes the search for novel antibacterially active substances an urgent task (Chemistry & Industry 1997, 131; Drug Discovery Today, 1997, 47). The antibacterial activity of nematophin and its known derivatives is not entirely satisfactory.

The present invention provides

1. Compounds of the general formula (I)

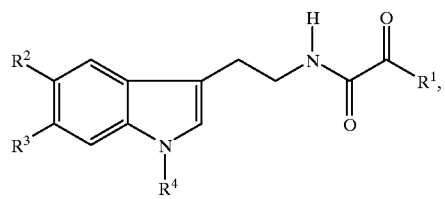

in which
- $R^1$ represents optionally branched $C_1$–$C_8$-alkyl or $C_4$–$C_8$-cycloalkyl,
- $R^2$ independently of $R^3$ represents hydrogen, $C_1$–$C_4$-alkyl, $C_1$–$C_4$-alkoxy, $C_1$–$C_4$-thioalkyl, phenyl or halogen,
- $R^3$ represents hydrogen, $C_1$–$C_4$-alkyl or halogen and
- $R^4$ represents optionally branched $C_1$–$C_6$-alkyl, $C_4$–$C_6$-cycloalkyl, phenyl which is optionally mono- to trisubstituted by $C_1$–$C_3$-alkyl, $C_1$–$C_3$-alkoxy, $C_1$–$C_3$-thioalkyl, halogen, nitro or amino or benzyl which is optionally mono- to trisubstituted by $C_1$–$C_3$-alkyl, $C_1$–$C_3$-alkoxy, $C_1$–$C_3$-thioalkyl, halogen, nitro or amino.

The compounds of the general formula (I) can be present in the form of their racemates or as enantiomerically pure compounds and in the form of their pharmaceutically utilizable hydrates and acid addition salts.

2. Process for preparing compounds of the general formula (I)

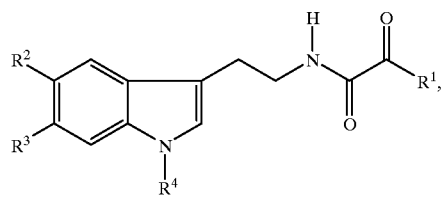

in which
- $R^1$ represents optionally branched $C_1$–$C_8$-alkyl or $C_4$–$C_8$-cycloalkyl,
- $R^2$ independently of $R^3$ represents hydrogen, $C_1$–$C_4$-alkyl, $C_1$–$C_4$-alkoxy, $C_1$–$C_4$-thioalkyl, phenyl or halogen,
- $R^3$ represents hydrogen, $C_1$–$C_4$-alkyl or halogen and
- $R^4$ represents optionally branched $C_1$–$C_6$-alkyl, $C_4$–$C_6$-cycloalkyl, phenyl which is optionally mono- to trisubstituted by $C_1$–$C_3$-alkyl, $C_1$–$C_3$-alkoxy, $C_1$–$C_3$-thioalkyl, halogen, nitro or amino or benzyl which is optionally mono- to trisubstituted by $C_1$–$C_3$-alkyl, $C_1$–$C_3$-alkoxy, $C_1$–$C_3$-thioalkyl, halogen, nitro or amino, characterized in that substituted indoles of the formula (II)

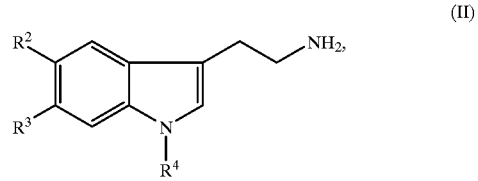

in which
$R^2$, $R^3$, $R^4$ are as defined above
are reacted with α-ketocarboxylic acid derivatives of the formula (III)

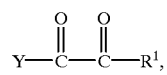

in which
Y represents OH or halogen and
$R^1$ is as defined above,
if appropriate in the presence of an acid binder and if appropriate in the presence of a diluent.

Compared to the known representatives of this structure type, the compounds of the general formula (I) according to the invention surprisingly have considerably higher antibacterial activity. They are therefore suitable for use as antibacterially active compounds for human and veterinary medicine.

Preference is given to compounds of the formula (I) in which
- $R^1$ represents optionally branched $C_1$–$C_6$-alkyl or $C_4$–$C_6$-cycloalkyl,
- $R^2$ independently of $R^3$ represents hydrogen, $C_1$–$C_2$-alkyl, $C_1$–$C_2$-alkoxy, $C_1$–$C_2$-thioalkyl, phenyl, fluorine, chlorine or bromine,
- $R^3$ represents hydrogen, $C_1$–$C_2$-alkyl, fluorine or bromine and
- $R^4$ represents optionally branched $C_1$–$C_4$-alkyl, $C_4$–$C_6$-cycloalkyl, phenyl which is optionally mono- to trisubstituted by $C_1$–$C_2$-alkyl, $C_1$–$C_2$-alkoxy, fluorine, chlorine, bromine, nitro or amino or benzyl which is optionally mono- to trisubstituted by $C_1$–$C_2$-alkyl, $C_1$–$C_2$-alkoxy, fluorine, chlorine, bromine, nitro or amino, and their pharmaceutically utilizable hydrates and acid addition salts.

Particular preference is given to compounds of the formula (I) in which $R^1$ represents optionally branched $C_1$–$C_6$-alkyl or $C_4$–$C_6$-cycloalkyl, $R^2$ independently of $R^3$ represents hydrogen, $C_1$–$C_2$-alkyl, $C_1$–$C_2$-alkoxy, fluorine or chlorine, $R^3$ represents hydrogen, $C_1$–$C_2$-alkyl, fluorine or chlorine and $R^4$ represents optionally branched $C_1$–$C_4$-alkyl, $C_4$–$C_6$-cycloalkyl, phenyl which is optionally mono- or disubstituted by $C_1$–$C_2$-alkyl, $C_1$–$C_2$-alkoxy, fluorine, chlorine, nitro or amino or benzyl which is optionally mono- or disubstituted by $C_1$–$C_2$-alkyl, $C_1$–$C_2$-alkoxy, fluorine, chlorine, nitro or amino, and their pharmaceutically utilizable hydrates and acid addition salts.

Very particular preference is given to compounds of the formula (I) in which $R^1$ represents branched alkyl having up to 4 C atoms, $R^2$ and $R^3$ represent hydrogen, $R^4$ represents $C_1$–$C_4$-alkyl, phenyl or benzyl.

The process according to the invention for preparing the compounds of the formula (I) by reacting the compounds of the formula (II) with α-ketocarboxylic acid derivatives of the formula (III) where Y is chlorine can be represented by the following reaction scheme:

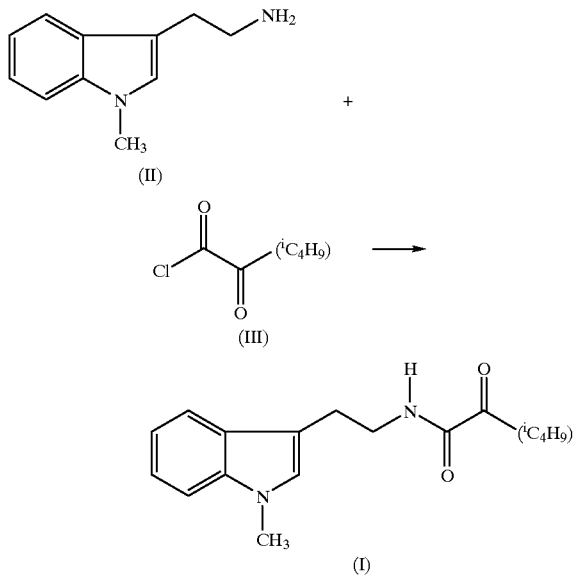

The compounds of the formula (II) are known (for example J. Med. Chem. 37 (1994) 4307–4316) or can be prepared by known methods. Examples of compounds (II) which may be mentioned are:

1-methyl-3-(2-aminoethyl)-indole,
1-ethyl-3-(2-aminoethyl)-indole,
1-propyl-3-(2-aminoethyl)-indole,
1-isopropyl-3-(2-aminoethyl)-indole,
1-cyclopentyl-3-(2-aminoethyl)-indole,
1-phenyl-3-(2-aminoethyl)-indole,
1-benzyl-3-(2-aminoethyl)-indole,
1-(4-chlorobenzyl)-3-(2-aminoethyl)-indole,
1-(2,6-dichlorobenzyl)-3-(2-aminoethyl)-indole.

The compounds of the formula (III) are likewise known, and some of them are commercially available. Compounds of the formula (III) where Y is halogen, such as, for example, chlorine, can be prepared from compounds of the formula (III) where Y is OH according to known methods by reaction with halogenating agents such as, for example, with thionyl chloride or oxalyl chloride. Examples of compounds (III) where Y is OH which may be mentioned are:

pyruvic acid,
2-oxo-butyric acid,
2-oxo-valeric acid,
2-oxo-4-methyl-valeric acid,
2-oxo-3-methyl-valeric acid,
cyclobutyl-glyoxylic acid,
cyclopentyl-glyoxylic acid,
cyclohexyl-glyoxylic acid.

If the starting materials used are compounds of the formula (III) where Y is chlorine, the preparation of the compounds of the formula (I) is carried out in an inert solvent in the presence of an acid scavenger. Suitable solvents are, for example, halogenated hydrocarbons, such as, for example, methylene chloride, chloroform, carbon tetra-chloride, aliphatic or aromatic hydrocarbons, such as, for example, toluene, polar inert solvents, such as, for example, dimethylformamide, N-methylpyrrolidone, dimethyl sulphoxide or su ipholane. It is also possible to use mixtures of these solvents.

Suitable acid scavengers are customary acid binders such as, for example, alkali metal or alkaline earth metal carbonates, trimethylamine, triethylamine, tributylamine, 1,4-diazabicyclo [2.2.2] octane (DABCO), 1,8-diazabicyclo [5.4.0]undec-7-ene (DBU) or pyridine.

The acid scavengers used are generally employed in an amount of from 80 to 200 mol %, based on the molar amount of the compound (III) where Y is chlorine. Preference is given to using an amount of from 110 to 150 mol %.

It is also possible to carry out the reaction in a large excess of pyridine which then acts simultaneously as solvent and acid scavenger.

The compounds of the formula (II) and (III) are generally employed in approximately equimolar amounts.

In this procedure, the reaction temperatures can be varied between −20 and 80° C. Preference is given to working between −10° C. and 25° C.

The reaction can be carried out at atmospheric pressure, but also under elevated pressure. In general, the reaction is carried out at pressures between 1 bar and 100 bar, preferably between 1 and 10 bar.

If the starting materials used are compounds of the formula (III) where Y is OH, the reaction is carried out in an inert solvent in the presence of an auxiliary which is customary for forming amide bonds. Suitable solvents are the solvents mentioned above such as, for example, methylene chloride, chloroform, dimethylformamide or N-methylpyrrolidoine. It is also possible to use mixtures of these solvents.

Suitable auxiliaries are, for example , N'-(3-dimethylaminopropyl)-N-ethylcarbo-diimide (EDC) or dicyclohexylcarbodiimide (DCC).

Suitable auxiliaries for forming the amide bond are, for example, hydroxybenzotriazole in the presence of an organic base such as, for example, triethylamine, tributylamine or N-methylmorpholine. The starting materials of the formula (II) and (III) are employed in approximately equimolar amounts. The auxiliaries are employed in approximately equimolar amounts, based on the compound of the formula (III).

In this procedure, the reaction temperatures can be varied between −20 and 80° C. The reaction is preferably carried out between −10° C. and 25° C.

The reaction can be carried out at atmospheric pressure, but also under elevated pressure. In general, the reaction is carried out at pressures between 1 bar and 100 bar, preferably between 1 and 10 bar.

After the reaction has ended, the resulting compounds of the formula (I) are purified by customary methods of organic chemistry, for example by crystallization or chromatography.

The acid addition salts of the compounds according to the invention are prepared in a customary manner, for example by dissolving the compounds in a sufficient quantity of aqueous acid and precipitating the salt with a water-miscible organic solvent such as methanol, ethanol, acetone, acetonitrile. It is also possible to dissolve equivalent amounts of the compound according to the invention and acid in water, followed by evaporation to dryness or filtering off with suction of the precipitated salt.

The compounds according to the invention have strong antibiotic action and very good activity against gram-positive microorganisms, specifically staphylococci.

Owing to these useful properties, they can be used as chemotherapeutically active compounds in medicine and veterinary medicine and as substances for preserving inorganic and organic materials, in particular organic materials of all types, for example polymers, lubricants, dyes, fibres, leather, paper and wood, of foodstuffs and of water.

With the aid of the compounds according to the invention, it is possible to control gram-positive bacteria, in particular staphylococci, and bacteria-like microorganisms, and to prevent, ameliorate and/or cure the disorders caused by these pathogens.

Even against bacteria which are classified as less sensitive to other antibacterial agents, in particular resistant Staphylococcus aureus, the compounds according to the invention show surprising activity increases.

The compounds according to the invention are particularly active against bacteria and bacteria-like microorganisms. They are therefore particularly suitable for the prophylaxis and chemotherapy of local and systemic infections in human and veterinary medicine which are caused by these pathogens.

The compounds are furthermore suitable for controlling protozoonoses and helminthoses.

The compounds according to the invention can be administered in various pharmaceutical preparations. Preferred pharmaceutical preparations which may be mentioned are tablets, coated tablets, capsules, pills, granules, suppositories, injections and orally administerable solutions, suspensions and emulsions, and furthermore pastes, ointments, gels, creams, lotions, powders and sprays.

The active compounds are preferably suitable for controlling bacterial disorders which occur in animal keeping and animal breeding with productive, breeding, zoo, laboratory and experimental animals and pets. They are active here against all or individual stages of development, and against resistant and normally sensitive strains. By controlling the bacterial disorders, disease, cases of death and yield reductions (for example in the production of meat, milk, wool, hides, eggs, honey, etc.) should be decreased, so that more economical and simpler animal keeping is possible owing to the use of the active compounds.

The productive and breeding animals include mammals such as, for example, cattle, horses, sheep, pigs, goats, camels, water buffalo, donkeys, rabbits, fallow deer, reindeer, fur-bearing animals such as, for example, mink, chinchilla and raccoons, birds such as, for example, chickens, geese, turkeys, ducks, doves and species of birds for keeping at home and in zoos. They further include productive and ornamental fish.

The laboratory and experimental animals include mice, rats, guinea-pigs, golden hamsters, dogs and cats.

In general, it has proven advantageous to administer amounts of approximately 0.5 to approximately 50 mg, preferably 1 to 20 mg, of active compound per kg of body weight per day to achieve effective results.

The active compounds can also be administered together with the feed or drinking water of the animals.

Feed and foodstuffs contain 0.01 to 100 ppm, preferably 0.5 to 50 ppm, of the active compound in combination with suitable edible material.

Such a feed or foodstuff can be used both for healing purposes and for prophylactic purposes.

The preparation of such a feed or foodstuff is carried out by mixing a concentrate or a premix which contains 0.5 to 30%, preferably 1 to 20%, by weight of an active compound in a mixture with an edible- organic or inorganic carrier with customary feeds. Edible carriers are, for example, maize flour or maize and soya bean flour or mineral salts which preferably contain a small amount of an edible dust-preventing oil, for example maize oil or soya bean oil. The premixture obtained in this way can then be added to the complete feed before feeding it to the animals.

The minimum inhibitory concentrations (MIC) of the compounds according to the invention were determined by serial dilution methods on iso-sensitest agar (Oxoid). For each test substance, a number of agar plates were prepared which, each with a doubled dilution, contained decreasing concentrations of the active compound. The agar plates were inoculated using a multipoint inoculator (Denley). For inoculation, overnight cultures of the pathogens were used which had previously been diluted such that each inoculation point contained about $10^4$ colony-forming particles. The inoculated agar plates were incubated at 37° C., and the bacterial growth was read off after about 20 hours. The MIC value ($\mu g/ml$) indicates the lowest active compound concentration at which no growth could be detected with the naked eye.

In the table below, the MIC values of some of the compounds according to the invention are listed. The following compounds A and B, known from U.S. Pat. No. 5,569,608, are listed as reference compounds.

Comparative compound A

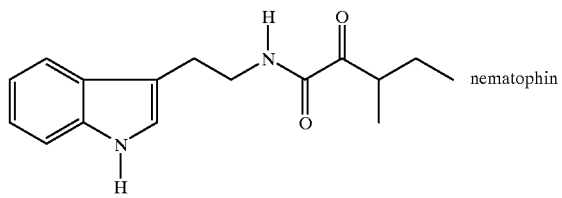

nematophin

Comparative compound B

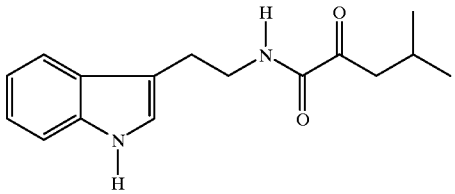

TABLE

| | | Comparative compound | | Compounds according to the invention | | | | | |
|---|---|---|---|---|---|---|---|---|---|
| | | MIC values (μg/ml) | | | | | | | |
| Species | Strain | A | B | 1 | 2 | 3 | 4 | 5 | 6 |
| *Staph. aureus* | ATCC 6538 | 0.25 | 0.125 | 0.015 | 0.03 | 0.03 | 0.125 | 0.03 | 0.125 |
| | ATCC 25923 | 0.125 | 0.25 | 0.015 | 0.03 | 0.03 | 0.06 | 0.06 | 0.125 |
| | ATCC 29213 | 0.125 | 0.25 | 0.015 | 0.03 | 0.03 | 0.25 | 0.06 | 0.125 |
| *Staph. interm.* | ATCC 29663 | 8 | 2 | 2 | 2 | 4 | 2 | 1 | 8 |
| *Staph. hyicus* | 9621* | 1 | 0.25 | 0.06 | 0.03 | 1 | 0.06 | 0.06 | 1 |
| | 9622* | 0.5 | 0.03 | 0.06 | 0.03 | 0.5 | 0.25 | 0.015 | 1 |
| | 9637* | 0.25 | 0.25 | 0.015 | 0.03 | 0.03 | 0.125 | 0.06 | 0.125 |
| | 9641* | 0.25 | 0.25 | 0.015 | 0.03 | 0.03 | 0.125 | 0.06 | 0.125 |

*actual clinical isolates

PREPARATION OF THE ACTIVE COMPOUNDS

Example 1

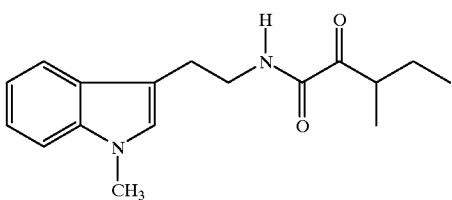

At 0° C. and with ice-cooling, 0.9 g of 2-oxo-3-methyl-valeryl chloride are added dropwise to a solution of 1 g of 1-methyltryptamine in 5 ml of pyridine. The mixture is allowed to warm to room temperature and is stirred overnight. The reaction mixture is then mixed with water and extracted three times with ether. The organic phase is extracted successively with saturated ammonium chloride solution, 5% strength aqueous sodium hydroxide solution, water and saturated sodium chloride solution, dried over sodium sulphate and concentrated under reduced pressure. The resulting residue is chromatographed over silica gel (methylene chloride/methanol 99:1). This gives 0.31 g of an oily product.

$^1$H-NMR (400 MHz, CDCl$_3$): δ=0.88 (t, 3H), 1.09 (d, 3H), 1.35–1.45 (m, 1H), 1.57–1.68 (m, 1H), 1.95–2.05 (m, 1H), 2.93–3.03 (m, 2H), 3.55–3.63 (m, 2H), 3.75 (s, 3H), 5.53 (s, brd, 1H), 6.87 (s, 1H), 7.12 (m, 1H), 7.25 (m, 1H), 7.32 (m, 1H), 7.6 (m, 1H) ppm.
MS/EI (−70 eV): m/e=286(M+, 5%), 157 (32%), 144 (100%).

Example 2

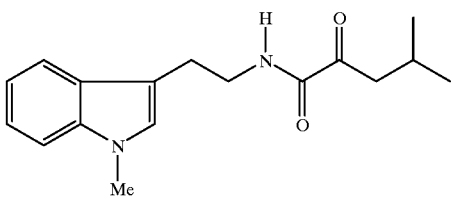

At −30° C., 1.34 g of 1-hydroxy-1H-benzotriazole hydrate (HOBT) and 1.68 g of N'-(3-dimethylaminopropyl)-N-ethylcarbodiimide hydrochloride (EDC) are added to a solution of 0.91 g of 4-methyl-2-oxo-valeric acid in 40 ml of DMF. The mixture is stirred for half an hour, and a solution of 1.22 g of 1-methyl-tryptamine in 5 ml of DMF is then added. Triethylamine is then added such that a pH of about 9 results. The mixture is stirred at 0° C. for 1 hour, then allowed to warm to room temperature and stirred overnight at room temperature. The reaction mixture is concentrated under reduced pressure and the residue is taken up in ethyl acetate. The solution is extracted successively with water, aqueous Na$_2$CO$_3$ solution and saturated aqueous sodium chloride solution, dried over sodium sulphate and concentrated under reduced pressure. The residue is chromatographed over silica gel (methylene chloride/ methanol 99:1). This gives 1.34 g of a viscous oil.

$^1$H-NMR (400 MHz, CDCl$_3$): δ=0.94 (d, J=6.6 Hz; 6H), 2.1–2.2 (m; 1H), 2.79 (d, J=6.8 Hz; 2H), 3.0 (m; 2H), 3.58–3.63 (m; 2H), 3.76 (s; 3H), 6.89 (s; 1H), 7.05 (m, brd; 1H), 7.1 (m; 1H), 7.23 (m; 1H), 7.3 (m; 1H), 7.58 (m; 1H) ppm.

Example 3

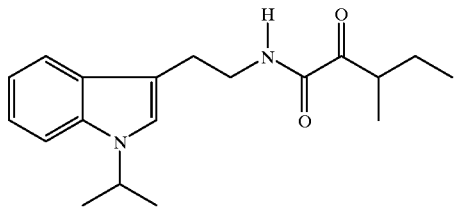

Analogously to the procedure of Example 2, 0.53 g of the title compound are prepared as an oil from 0.91 g of 3-methyl-2-oxovaleric acid and 1.43 g of 1-isopropyl-tryptamine.

$^1$H-NMR (400 MHz, CDCl$_3$): δ=0.88 (t, 3H), 1.1 (d, 3H), 1.35–1.45 (m, 1H), 1.52 (d, 6H), 1.67–1.78 (m, 1H), 3.02 (m, 2H), 3.47–3.55 (m, 1H), 3.63 (m, 2H), 4.6–4.7 (m, 1H), 7.03 (s, brd, 1H), 7.07 (s, 1H), 7.12 (m, 1H), 7.22 (m, 1H), 7.37 (m, 1H), 7.59 (m, 1H) ppm.

Example 4

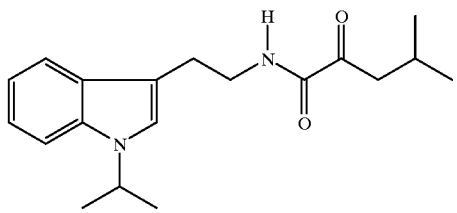

Analogously to the procedure of Example 2, 0.5 g of product are prepared in the form of a viscous oil from 0.91 g of 4-methyl-2-oxovaleric acid and 1.43 g of 1-isopropyl-tryptamine.
$^1$H-NMR (400 MHz, CDCl$_3$): δ=0.94 (d, 6H), 1.52 (d, 6H), 2.1–2.2 (m, 1H), 2.8 (d, 2H), 3.0 (m, 2H), 3.62 (m, 2H), 4.6–4.7 (m, 1H), 7.03 (s, brd, 1H), 7.07 (s, 1H), 7.12 (m, 1H), 7.22 (m, 1H), 7.37 (m, 1H), 7.58 (m, 1H) ppm.

Example 5

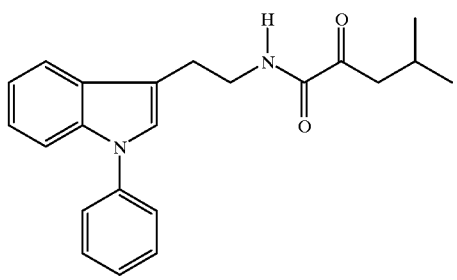

Analogously to the procedure of Example 2, 0.53 g of product are prepared from 0.65 g of 4-methyl-2-oxovaleric acid and 1.2 g of 1-phenyl-tryptamine.
$^1$ H-NMR (400 MHz, CDCl$_3$): δ=0.94 (d, J=6.6 Hz; 6H), 2.1–2.2 (m; 1H), 2.80 (d, J=7 Hz; 2H), 3.04–3.1 (m; 2H), 3.65–3.72 (m, 2H), 7.12 (m, brd; 1H), 7.17–7.28 (m; 3H), 7.32–7.38 (m; 1H), 7.47–7.55 (m; 4H), 7.58 (m; 1H), 7.67 (m; 1H) ppm.

Example 6

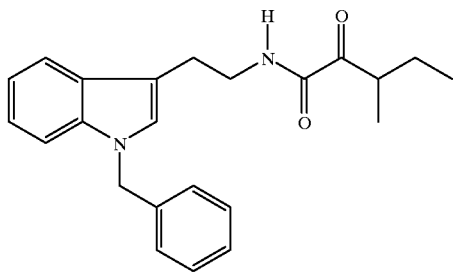

Analogously to the procedure of Example 2, 1.43 g of the oily product are obtained from 0.91 g of 3-methyl-2-oxovaleric acid and 1.75 g of 1-benzyl-tryptamine.
$^1$H-NMR (400 MHz, CDCl$_3$): δ=0.86 (t, 3H), 1.08 (d, 3H), 1.33–1.43 (m, 1H), 1.65–1.75 (m, 1H), 3.01 (m, 2H), 3.45–3.55 (m, 1H), 3.63 (m, 2H), 5.29 (s, 2H), 6.97 (s, 1H), 7.05 (s, brd, 1H), 7.12 (m, 3H), 7.18 (m, 1H), 7.23–7.35 (m, 4H), 7.62 (m, 1H)

Example 7

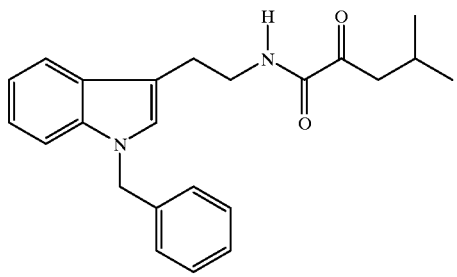

Analogously to the procedure of Example 2, 1.08 g of product are obtained from 0.91 g of 4-methyl-2-oxovaleric acid and 1.75 g of 1-benzyl-tryptamine.
Melting point: 82–3° C.
$^1$H-NMR (400 MHz, CDCl$_3$): δ=0.93 (d, 6H), 2.1–2.2 (m, 1H), 2.78 (d, 2H), 3.0 (m, 2H), 3.62 (m, 2H), 5.29 (s, 2H), 6.96 (s, 1H), 7.05 (s, brd, 1H), 7.12 (m, 3H), 7.2 (m, 1H), 7.25–7.35 (m, 4H), 7.6 (m, 1H) ppm.

What is claimed is:
1. A compound of the general formula (I)

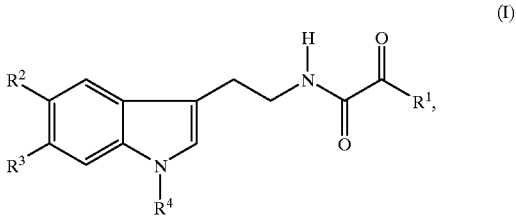

(I)

in which
  $R^1$ represents optionally branched C$_1$–C$_8$-alkyl or C$_4$–C$_8$-cycloalkyl,
  $R^2$ independently of $R^3$ represents hydrogen, C$_1$ –C$_4$-alkyl, C$_1$–C$_4$-alkoxy, C$_1$–C$_4$-thioalkyl, phenyl or halogen,
  $R^3$ represents hydrogen, C$_1$–C$_4$-alkyl or halogen and
  $R^4$ represents optionally branched C$_1$–C$_6$-alkyl, C$_4$–C$_6$-cycloalkyl, phenyl which is optionally mono- to trisubstituted by C$_1$–C$_3$-alkyl, C$_1$–C$_3$-alkoxy, C$_1$–C$_3$-thioalkyl, halogen, nitro or amino or benzyl which is optionally mono- to trisubstituted by C$_1$–C$_3$-alkyl, C$_1$–C$_3$-alkoxy, C$_1$–C$_3$-thioalkyl, halogen, nitro or amino, in the form of its racemate or enantiomerically pure compound and in the form of its pharmaceutically utilizable hydrate or acid addition salt.

2. Process for preparing compounds of the general formula (I)

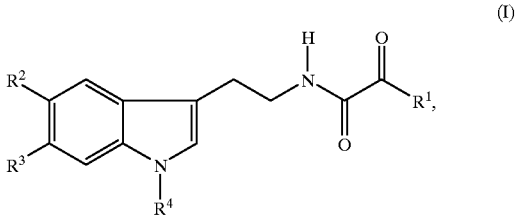

(I)

in which
  $R^1$ represents optionally branched C$_1$–C$_8$-alkyl or C$_4$–C$_8$-cycloalkyl, $R^2$ independently of $R^3$ represents hydrogen, $C_1$–$C_4$-alkyl, $C_1$–$C_4$-alkoxy, $C_1$–$C_4$-thioalkyl, phenyl or halogen, $R^3$ represents hydrogen, $C_1$–$C_4$-alkyl or halogen and $R^4$ represents optionally branched $C_1$–$C_6$-alkyl, $C_4$–$C_6$-cycloalkyl, phenyl which is optionally mono- to trisubstituted by $C_1$–$C_3$-alkyl, $C_1$–$C_3$-alkoxy, $C_1$–$C_3$-thioalkyl, halogen, nitro or amino or benzyl which is optionally mono- to trisubstituted by $C_1$–$C_3$-alkyl, $C_1$–$C_3$-alkoxy, $C_1$–$C_3$-thioalkyl, halogen, nitro or amino, characterized in that substituted indoles of the formula (II)

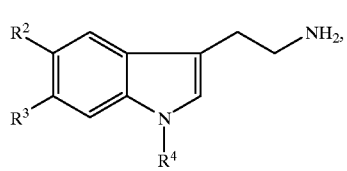

(II)

in which $R^2$, $R^3$, $R^4$ are as defined above are reacted with α-ketocarboxylic acid derivatives of the formula (III)

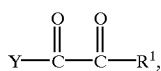

(III)

in which

Y represents OH or halogen, $R^1$ is as defined above, optionally in the presence of an acid binder and optionally in the presence of a diluent.

3. A compound of the formula (I) according to claim 1, in which $R^1$ represents optionally branched $C_1$–$C_6$-alkyl or $C_4$–$C_6$-cycloalkyl, $R^2$ independently of $R^3$ represents hydrogen, $C_1$–$C_2$-alkyl, $C_1$–$C_2$-alkoxy, $C_1$–$C_2$-thioalkyl, phenyl, fluorine, chlorine or bromine, $R^3$ represents hydrogen, $C_1$–$C_2$-alkyl, fluorine or bromine and $R^4$ represents optionally branched $C_1$–$C_4$-alkyl, $C_4$–$C_6$-cycloalkyl, phenyl which is optionally mono- to trisubstituted by $C_1$–$C_2$-alkyl, $C_1$–$C_2$-alkoxy, fluorine, chlorine, bromine, nitro or amino or benzyl which is optionally mono- to trisubstituted by $C_1$–$C_2$-alkyl, $C_1$–$C_2$-alkoxy, fluorine, chlorine, bromine, nitro or amino, or its pharmaceutically utilizable hydrate or acid addition salt.

4. A compound of the formula (I) according to claim 1, in which $R^1$ represents optionally branched $C_1$–$C_6$-alkyl or $C_4$–$C_6$-cycloalkyl, $R^2$ independently of $R^3$ represents hydrogen, $C_1$–$C_2$-alkyl, $C_1$–$C_2$-alkoxy, fluorine, chlorine or bromine, $R^3$ represents hydrogen, $C_1$–$C_2$-alkyl, fluorine or chlorine and $R^4$ represents optionally branched $C_1$–$C_4$-alkyl, $C_4$–$C_6$-cycloalkyl, phenyl which is optionally mono- or disubstituted by $C_1$–$C_2$-alkyl, $C_1$–$C_2$-alkoxy, fluorine, chlorine, nitro or amino or benzyl which is optionally mono- or disubstituted by $C_1$–$C_2$-alkyl, $C_1$–$C_2$-alkoxy, fluorine, chlorine, nitro or amino, or its pharmaceutically utilizable hydrate or acid addition salt.

5. A pharmaceutically composition comprising a compound of the formula (I) according to claim 1.

6. A process for preparing a pharmaceutical composition comprising formulating the compound of the formula (I) according to claim 1 and optionally a pharmaceutically utilizable carrier.

7. A process for preparing an antibacterial composition comprising formulating the compound of the formula (I) according to claim 1 and optionally a carrier.

* * * * *